(12) United States Patent
Schmidt et al.

(10) Patent No.: US 10,395,365 B2
(45) Date of Patent: Aug. 27, 2019

(54) METHOD, COMPUTER AND IMAGING APPARATUS FOR DETERMINING AN IMAGING PARAMETER FOR AN IMAGING PROCEDURE

(71) Applicant: Siemens Healthcare GmbH, Erlangen (DE)

(72) Inventors: Bernhard Schmidt, Fuerth (DE); Thomas Flohr, Uehlfeld (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/783,086

(22) Filed: Oct. 13, 2017

(65) Prior Publication Data
US 2018/0108128 A1    Apr. 19, 2018

(30) Foreign Application Priority Data

Oct. 14, 2016    (DE) .......................... 10 2016 220 093

(51) Int. Cl.
| | |
|---|---|
| *G06K 9/62* | (2006.01) |
| *G06T 7/00* | (2017.01) |
| *G16H 30/20* | (2018.01) |
| *G16H 40/63* | (2018.01) |
| *G01R 33/54* | (2006.01) |

(52) U.S. Cl.
CPC .......... *G06T 7/0012* (2013.01); *G06K 9/6269* (2013.01); *G16H 30/20* (2018.01); *G16H 40/63* (2018.01); *G01R 33/543* (2013.01); *G06T 2207/30168* (2013.01)

(58) Field of Classification Search
CPC combination set(s) only.
See application file for complete search history.

(56) References Cited

U.S. PATENT DOCUMENTS

| | | | |
|---|---|---|---|
| 9,471,987 B2 * | 10/2016 | Harder | ................. G06K 9/3233 |
| 10,074,037 B2 * | 9/2018 | Lu | ........................... G06N 20/00 |
| 2007/0055153 A1 * | 3/2007 | Simopoulos | ............. A61B 8/00 600/437 |

(Continued)

FOREIGN PATENT DOCUMENTS

DE    102014102080 A1    8/2015

*Primary Examiner* — Tsung Yin Tsai
(74) *Attorney, Agent, or Firm* — Schiff Hardin LLP (57) ABSTRACT

In a method and computer for determining an imaging parameter for an imaging procedure, a patient-specific imaging value for imaging an image data set is provided to a computer. An imaging parameter is determined in the computer by applying a trained imaging rule to the patient-specific imaging value. The trained imaging rule is based on a number of training data sets, wherein the training data sets each includes at least one patient-specific training imaging value and at least one training imaging parameter and at least one training quality evaluation. The complex influences of the patient-specific imaging values and the imaging parameters on the result of imaging can be quantified thereby. Allocation of the training quality evaluation by individual operators or specific groups of operators makes it possible to adjust the image recording parameters flexibly and individually. The imaging parameter can be determined such that the result of imaging is individually adjusted to an operator.

17 Claims, 5 Drawing Sheets

(56) References Cited

U.S. PATENT DOCUMENTS

| | | | |
|---|---|---|---|
| 2009/0069668 A1* | 3/2009 | Stemmer | A61B 5/055 600/413 |
| 2012/0190962 A1* | 7/2012 | Glaser-Seidnitzer | A61B 6/032 600/407 |
| 2012/0236995 A1* | 9/2012 | Eusemann | A61B 6/03 378/108 |
| 2015/0260819 A1 | 9/2015 | Lauer et al. | |
| 2015/0367145 A1 | 12/2015 | Sjolund et al. | |
| 2016/0129282 A1 | 5/2016 | Yin et al. | |
| 2017/0083682 A1 | 3/2017 | McNutt et al. | |
| 2017/0351937 A1* | 12/2017 | Lu | G06N 20/00 |

* cited by examiner

METHOD, COMPUTER AND IMAGING APPARATUS FOR DETERMINING AN IMAGING PARAMETER FOR AN IMAGING PROCEDURE

BACKGROUND OF THE INVENTION

Field of the Invention

The present invention concerns a method and a computer for determining an imaging parameter for an imaging procedure to be conducted by an imaging apparatus, in particular a medical imaging apparatus.

Description of the Prior Art

Numerous technical parameters (known as image recording parameters) have to be defined or set in different medical image recording apparatuses in order to achieve optimum examination results. These image recording parameters control data acquisition and/or image reconstruction and therefore influence the generated image data set. The image recording parameters can be defined by the choice of specified standard settings or protocols that are suitable for the intended examination. Furthermore, the individual technical parameters can also be set or changed by the operator.

In computerized tomography (CT for short) these image recording parameters relate, inter alia, to the voltage and current of the X-ray tubes used, settings for automatic dose modulation, speed of the table advance, thickness of the examined slices or parameters for image reconstruction. In magnetic resonance tomography (MR for short) these image recording parameters relate, inter alia, to the examination sequence used, the strength of the magnetic field or the frequency of the radiated radio-frequency field.

It is known to specify standard settings as protocols for image recording parameters as a function of the chosen type of examination at the factory at which the imaging apparatus is manufactured, and to supply them preset in the medical image recording apparatus. Specified types of examination in CT include, for example, imaging of a patient's head, imaging of a patient's lungs, angiography or three-phase CT for the liver. Specified types of examination in MR include, for example, real-time MR, MR spectroscopy or diffusion-weighted MR. If the image data set obtained with the specified standard settings does not meet the specific requirements of the operator in terms of quality, then the operator has to change the setting of the image recording parameters himself or herself, or with the assistance of a specialist.

The effects of a change in the image recording parameters on the attained quality of the image data set is very complex, however, and often cannot be appreciated by the operator, or only with considerable investigation. Therefore, the operator cannot change the image recording parameters efficiently and purposefully in order to increase the quality of the image data set. If image recording parameters are manually changed nevertheless, the changes caused thereby often do not lead to an improvement in the quality of the image data set. An adjustment of the parameters at the factory is possible only to a limited extent, since there are different requirements in terms of the quality of the image data set for different medical issues and operators. Compounding this is the fact that an operator can often only determine that the quality of the generated image data set does not meet expectations, but cannot give the reason (for example insufficient resolution, image artifacts) for the inadequate quality.

SUMMARY OF THE INVENTION

An object of the present invention is to provide a method that enables flexible and individual adjustment of the image recording parameters, in particular for the operator.

The inventive solution to the object will be described below in relation to different aspects of the invention (method, computer, imaging apparatus, data storage medium). Features, advantages and alternative embodiments mentioned in the context of one aspect are applicable to the other aspects. The functional features of the method and storage medium are formed by appropriate physical components of the computer and the imaging apparatus.

Furthermore, features, advantages or alternative embodiments, which are described below in conjunction with the training variables are applicable to the application variables, and vice versa. In particular, features, advantages or alternative embodiments of the patient-specific training imaging value should be transferred to the patient-specific imaging value and vice versa. In particular, features, advantages or alternative embodiments of the training imaging parameter should be transferred to the imaging parameter and vice versa. In particular, features, advantages or alternative embodiments of the training quality evaluation should be transferred to the quality evaluation and vice versa. In particular, features, advantages or alternative embodiments of a training image data set should be transferred to the image data set and vice versa. In particular, features, advantages or alternative embodiments of a training data set should be transferred to the result data set and vice versa.

The inventive method for determining an imaging parameter includes providing a computer with at least one patient-specific imaging value for imaging an image data set. Furthermore, the inventive method includes determining an imaging parameter in the computer by applying a trained imaging rule to the patient-specific imaging value, wherein the trained imaging rule is based on a number of training data sets, and wherein the training data sets each have at least one patient-specific training imaging value and at least one training imaging parameter and at least one training quality evaluation. The invention is based on the insight that by applying a trained imaging rule using training data sets, it is possible to quantify the complex influences of the patient-specific imaging values and imaging parameters on the result of imaging. It is consequently possible to adjust the image recording parameters flexibly and individually if the training quality evaluation is carried out by only one operator. In particular, the imaging parameter can be determined from the patient-specific imaging values such that the result of imaging is individually adjusted to an operator.

According to a further embodiment of the invention, an image data set is also recorded using the imaging parameter by operation of an imaging apparatus. For this image data set, a result data set is determined that includes a quality evaluation of the image data set and the patient-specific imaging value and the imaging parameter. This result data set is saved (stored). By saving the result data set, an additional data set underlying the training can be generated. This leads to more precise determining of the imaging rule.

According to a further embodiment of the invention, the trained imaging rule is also trained on the basis of the training data sets and the result data set. In particular, training of the trained imaging rule occurs in response to saving of the result data set. Renewed training of the imaging rule after any examination is capable of detecting time-related changes in the specific requirements of the operator in terms of quality. The trained imaging rule can therefore be adjusted thereto.

According to a further embodiment of the invention, the quality evaluation evaluates at least the quality of the image data set, the duration of imaging of the image data set and/or the radiation dose corresponding to imaging of the image data set of the patient. According to a further embodiment of the invention the training quality evaluation is a measure of the quality of a training image data set, the duration of imaging of the training image data set and/or the radiation dose corresponding to imaging of the training image data set of a patient. These three influencing factors decisively quantify the success of an examination and therefore are particularly suitable as a quality evaluation for training a self-learning system. Good image quality leads to no further imaging examinations being necessary, a short imaging duration leads to better utilization of the imaging device. A low radiation dose absorbed as a result of imaging of the image data set leads to less damage to patient tissue as a result of imaging. A quality evaluation or training quality evaluation determined by an operator is positive if the operator is predominantly satisfied with imaging of the image data set. A quality evaluation or training quality evaluation determined by an operator is negative if the operator is predominantly dissatisfied with imaging of the image data set.

According to a further embodiment of the invention, the quality evaluation and/or the training quality evaluation includes a discrete parameter that can only assume a finite number of values. An evaluation of imaging of the image data set by the use of a discrete scale correlates with the technical skills of an operator. In the case of evaluation using a continuous scale, a number of values matches the continuous scale of the same quality evaluation by the operator. This can have adverse effects on training of the trained imaging rule. A discrete scale can be, for example, marks, or an evaluation by means of words (such as, for example "unsuitable", "not very suitable", "somewhat suitable", "suitable"). A discrete scale can also be a color scale, in particular two or three colors of a traffic light, for example "red" and "green" or "red", "yellow" and "green".

According to a further embodiment of the invention, the discrete parameter can assume exactly two different values. In other words, the discrete parameter is a binary variable. This binary variable records the overall evaluation of imaging of the image data set and assumes values that represent "dissatisfied with imaging of the image data set" or "satisfied with imaging of the image data set". An operator often determines that imaging of the image data set does not meet requirements, but the operator cannot determine why imaging of the image data set does not meet requirements. However, with the inventive binary parameter, it is nevertheless possible for the operator to evaluate the imaging examination in this situation.

According to a further embodiment of the invention, the trained imaging rule is determined by a support vector machine, wherein data sets are sorted in the training phase according to the discrete parameter into at least one first and one second category, and wherein in the parameter space of all combinations of patient-specific imaging values and imaging parameters, at least one first hypersurface is determined which separates the first and the second categories. Furthermore, the trained imaging rule is determined at least by the first hypersurface. The parameter space is divided into two or more subspaces by the hypersurface. The anticipated quality evaluation, which an operator allocates for the combination of patient-specific imaging value and imaging parameter from this subspace, can be associated with each of these subspaces. On the basis of these subspaces an imaging parameter, which the operator will very likely deem satisfactory, can therefore be determined from the patient-specific imaging value.

According to a further embodiment of the invention, the imaging rule is determined by the hypersurface in such a way that it maps a patient-specific imaging value on the imaging parameter such that the spacing between the first hypersurface and a data point is extreme, wherein the data point has the patient-specific imaging value and the determined imaging parameter. Here, only imaging parameters are considered which can be set for imaging the image data set within the limits of the device specifications. In this case extreme means maximal if the data point is in a subspace which matches a quality evaluation that an operator awards to an image the operator deems satisfactory. By contrast, extreme means minimal if the data point is in a subspace which corresponds to a quality evaluation that an operator awards to an image the operator deems unsatisfactory. The probability of the result of imaging meeting the expectations of the operator is greatest as a result of this choice of imaging parameter since, in this way, the data points are located as far as possible in or as close as possible to the data points which promise a positive evaluation by the examining person.

Furthermore, the invention concerns a parameter-determining computer that determines an imaging parameter, the computer having an interface designed to receive a patient-specific imaging value, and a processor designed to determine an imaging parameter by applying a trained imaging rule to the patient-specific imaging value, wherein the trained imaging rule is based on a number of training data sets, wherein the training data sets each has at least one patient-specific training imaging value and at least one training imaging parameter and at least one training quality evaluation.

The parameter-determining computer thus is configured to implement the inventive method and its embodiments described above. The parameter-determining computer is designed to implement this method and its embodiments via the interface and the processor.

The invention also concerns an imaging apparatus having an image data acquisition scanner and an inventive parameter-determining computer.

The present invention also encompasses a non-transitory, computer-readable data storage medium encoded with programming instructions (program code) that, when the storage medium is loaded into a computer, cause the computer to implement any or all of the embodiments of the method according to the invention, as described herein.

A patient-specific imaging value is a parameter that is specified for imaging a patient and cannot be defined by the operator of the imaging apparatus. In other words, the patient-specific imaging value cannot be influenced by the operator, in particular the patient-specific imaging value is defined as early as before the start of imaging or recording. A patient-specific imaging value can relate to the design of the image recording scanner, the chosen type of examination, a suspected diagnosis, the examined organ, the gender of the examined patient, the weight of the examined patient and/or the age of the examined patient. If the patient-specific imaging value relates to a number of variables, then it can be represented as a vector. The patient-specific imaging value is not an image data set relating to the patient.

An imaging parameter is a parameter that can be set for the imaging apparatus for imaging of a patient therewith. An imaging parameter can relate to a data acquisition parameter and/or an image reconstruction parameter. A data acquisition parameter can relate to the tube voltage in a CT device, the tube current in a CT device, the automatic dose modulation, the table advance and/or the slice thickness. An image reconstruction parameter can relate to the convolution kernel of the image reconstruction algorithm or the window setting of the image reconstruction algorithm. If the imaging parameter relates to a number of variables it can, in particular, be represented as a vector.

An image data set designates one or more image(s) of a patient that have been determined by an imaging examination. These can be two-dimensional or three-dimensional images. An image data set resulting from a patient-specific imaging value and an imaging parameter designates an image data set that has been determined using this patient-specific imaging value and this imaging parameter.

A quality evaluation of an image data set is a parameter of the quality of a result of imaging which has been carried out using a patient-specific imaging value and an imaging parameter. A training quality evaluation of a training image data set is a parameter of the quality of the result of training imaging which has been carried out using a patient-specific training imaging value and a training imaging parameter. The quality of an image data set can be a measure of the resolution and/or contrast of the image data set. However, a quality evaluation can also relate to other parameters of the examination, for example its duration or examination dose used. In other words, a quality evaluation of an image data set can evaluate the circumstances of imaging of the image data set in addition to the image data set per se. A quality parameter can be a number but can also be a binary value. The binary value can map whether an operator is satisfied with the quality of the image data set. Furthermore, the quality parameter can be a vector with each vector evaluating a different aspect of the quality of an image data set.

A trained imaging rule is a function which maps a patient-specific imaging value on an imaging parameter and has been determined on the basis of a number of training data sets. The training data sets each include a patient-specific training imaging value, a training imaging parameter and a training quality evaluation. The training quality evaluation measures the quality of an image data set that has been determined using the patient-specific training imaging value and training imaging parameter. The trained imaging rule should map a patient-specific imaging value on an imaging parameter such that an image data set recorded with patient-specific imaging value and the determined imaging parameter will more likely meet the requirements of the operator (expressed by the quality evaluation).

A support vector machine (SVM for short) is a method for determining a hyperplane or a hypersurface in a parameter space of categorized training data sets, which hyperplane or hypersurface separates the individual categories of the training data sets. The hypersurface is determined such that the spacing of the data points located closest to the hypersurface is maximized. In general, a support vector machine can only determine hyperplanes; the training data sets are transferred into a higher-dimensional parameter space for determining a hypersurface. In this higher-dimensional parameter space a separating hyperplane can then be determined which with back transformation deforms to a hypersurface. The separating hyperplane can also be determined very efficiently in the higher-dimensional parameter space by applying a positive-definite kernel function. Hypersurfaces which do not separate the categories perfectly are obtained by introducing a slip parameter. An overadjustment to the training data sets can be avoided hereby. Support vector machines are known to those skilled in the art; further details thereof need not be explained herein, and reference can be made in this regard to the text by Ingo Steinwart, Andreas Christmann "Support Vector Machines" Springer (2008).

A parameter space is an (M+N)-dimensional vector space of all combinations or data sets of patient-specific imaging values and imaging parameters if the patient-specific imaging value is implemented by a vector having M entries, and the imaging parameter by a vector having N entries. If the patient-specific imaging value relates to just one variable, M is equal to 1. If the imaging parameter relates to just one variable, N is equal to 1. A determined combination or data set including a patient-specific imaging value and an imaging parameter corresponds to a point or a vector in the (M+N)-dimensional vector space of all combinations.

A category of training data sets corresponds to a volume of training data sets that have the same or a similar training quality evaluation. If the training quality parameter relates to a discrete parameter having a finite number of possible values, then there can be just as many categories as discrete values, and the training data sets can be associated with the categories according to the discrete parameter of the training quality evaluation. If the training quality parameter relates to a binary parameter, then there can only be two categories with which the training data sets can be associated according to the training quality parameters.

A subspace of a parameter space, which relates to a category of training data sets, is a subset of the parameter space, which predominantly contains only this category of training data sets. A subspace is not necessarily linear.

A hypersurface is a (M+N−1)-dimensional object in the (M+N)-dimensional parameter space of all combinations of patient-specific imaging values and imaging parameters. In a 2-dimensional parameter space a hypersurface corresponds, in particular, to a 1-dimensional, possibly curved line in this parameter space; in a 3-dimensionalen parameter space a hypersurface corresponds to a 2-dimensional, possibly curved surface in this parameter space. A hypersurface can be defined by an implicit function $$f(x_1, x_2, \ldots, x_M, y_1, y_2, \ldots, y_N) = 0$$

where the variables x correspond to the M entries of the vector of the patient-specific imaging value, and the variables y correspond to the N entries of the vector of the imaging parameter. A hypersurface has the property that it has two different sides, where for the one side f>0 applies, and for the other side f<0 applies. A hypersurface can separate two different subspaces. A hyperplane is a hypersurface whose defining implicit function is linear in all variables. A hyperplane is therefore an affine subspace of the parameter space.

DESCRIPTION OF THE PREFERRED EMBODIMENTS

Figure 1:
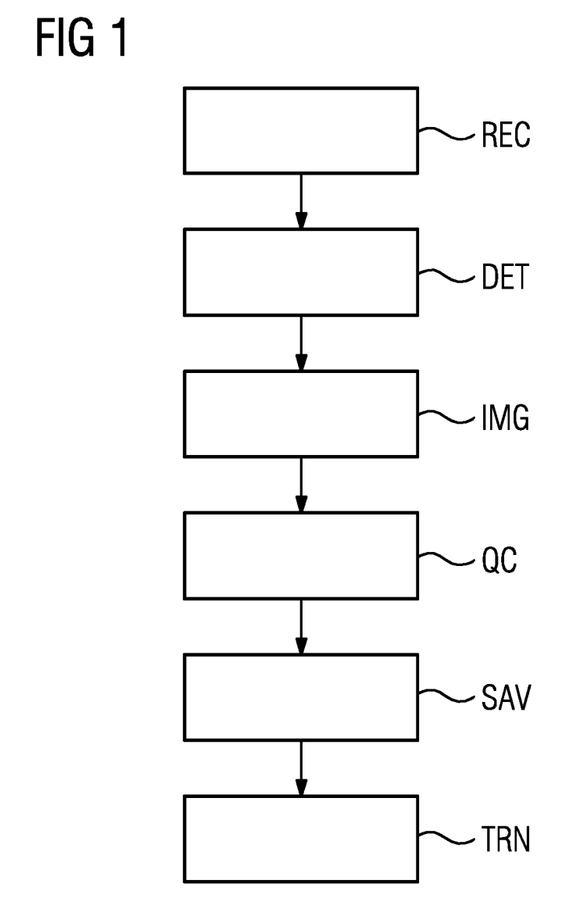
FIG. 1 is a flowchart of the method according to the invention for determining an imaging parameter.

FIG. 1 is a flowchart of a method for determining an imaging parameter.

The first step of the method is receiving REC a patient-specific imaging parameter via an interface 201 of a computer 200. In the illustrated method, a patient-specific imaging value is implemented by an operator at an input device 204, for example a keyboard. A patient-specific imaging value is, for example, the height, weight, gender or age of the patient. A patient-specific imaging value can also be an imaging region, i.e. a section of the patient that is to be imaged. Alternatively, it is possible to retrieve, the patient-specific imaging value from a database in which data relating to the patient 303 or relating to the imaging device 300 is saved. A number of patient-specific imaging values can also be input or be retrieved from a database or plurality of databases.

The next step of the method is determining DET an imaging parameter by applying a trained imaging rule to the patient-specific imaging value in the computer, wherein the trained imaging rule is based on a number of training data sets 207.1, 207.2, 207.3, wherein the training data sets 207.1, 207.2, 207.3 each include at least one patient-specific training imaging value 208.1, 208.2, 208.3 and at least one training imaging parameter 209.1, 209.2, 209.3 and at least one training quality evaluation 210.1, 210.2, 210.3. In the illustrated method the imaging rule has been determined by applying a support vector machine to the training data sets 207.1, 207.2, 207.3. A training quality evaluation 210.1, 210.2, 210.3 in the illustrated method is a binary parameter which maps whether the operator is satisfied or dissatisfied with the quality of the image data set 402, which has been determined by means of a patient-specific training imaging value 208.1, 208.2, 208.3 and a training imaging parameter 209.1, 209.2, 209.3. Using the training quality evaluation 210.1, 210.2, 210.3 the training data sets 207.1, 207.2, 207.3 are divided into two different categories, with the first category containing training data sets 207.1, 207.2, 207.3 of sufficient quality, and with the second category containing all training data sets 207.1, 207.2, 207.3 of insufficient quality. The quality can be evaluated by an operator. At least one hypersurface 509, 510 which separates the two categories is determined by applying a support vector machine. The training data sets 207.1, 207.2, 207.3 have been transformed here into a higher dimensional parameter vector space, and a separating hyperplane is determined in this. The separating hypersurface 509, 510 in the original parameter vector space then results due to the back transformation of the hyperplane in the higher dimensional parameter vector space into the original parameter vector space.

Based on the at least one hypersurface 509, 510, the imaging rule has been determined such that a patient-specific imaging value is mapped onto an imaging parameter in such a way that the spacing of the data point 512, 602 from the closest hyperplane 509, 510 in each case is extreme, with the data point including the patient-specific imaging value and the imaging parameter. A distinction is made as to whether there is even an imaging parameter for the patient-specific imaging value, so the resulting data point 512 is located in a subspace with data points having predominantly positive evaluations 509. If this is the case, the imaging parameter is determined in such a way that the spacing 513 of the data point 512 comprising the patient-specific imaging value and the determined imaging parameter from the closest hypersurface 509 in each case is maximal. If this is not the case, the imaging parameter is determined such that the spacing 603 of the data point 602 including the patient-specific imaging value and the determined imaging parameter from the closest hypersurface 509 in each case is minimal.

The spacing of a data point 512, 602 from a hypersurface 509, 510 is determined in this exemplary embodiment by the smallest radius of a hypersphere around the data point that the hypersurface 509, 510 touches but does not intersect. Further methods for determining spacing are known, for example the hypersurface 509, 510 can be triangulated, and the spacing from data point 512, 602 to the hypersurface is then the smallest spacing from a segment of the triangulated hypersurface. The data point 512, 602 with maximal or minimal spacing 513, 603 from a hypersurface 509, 510 is calculated in this exemplary embodiment by means of simulated cooling. The English term "simulated annealing" is also common for these methods. Other optimization methods, such as the great deluge algorithm or the ant colony optimization algorithm, are known, however, and can be used.

Figure 2:
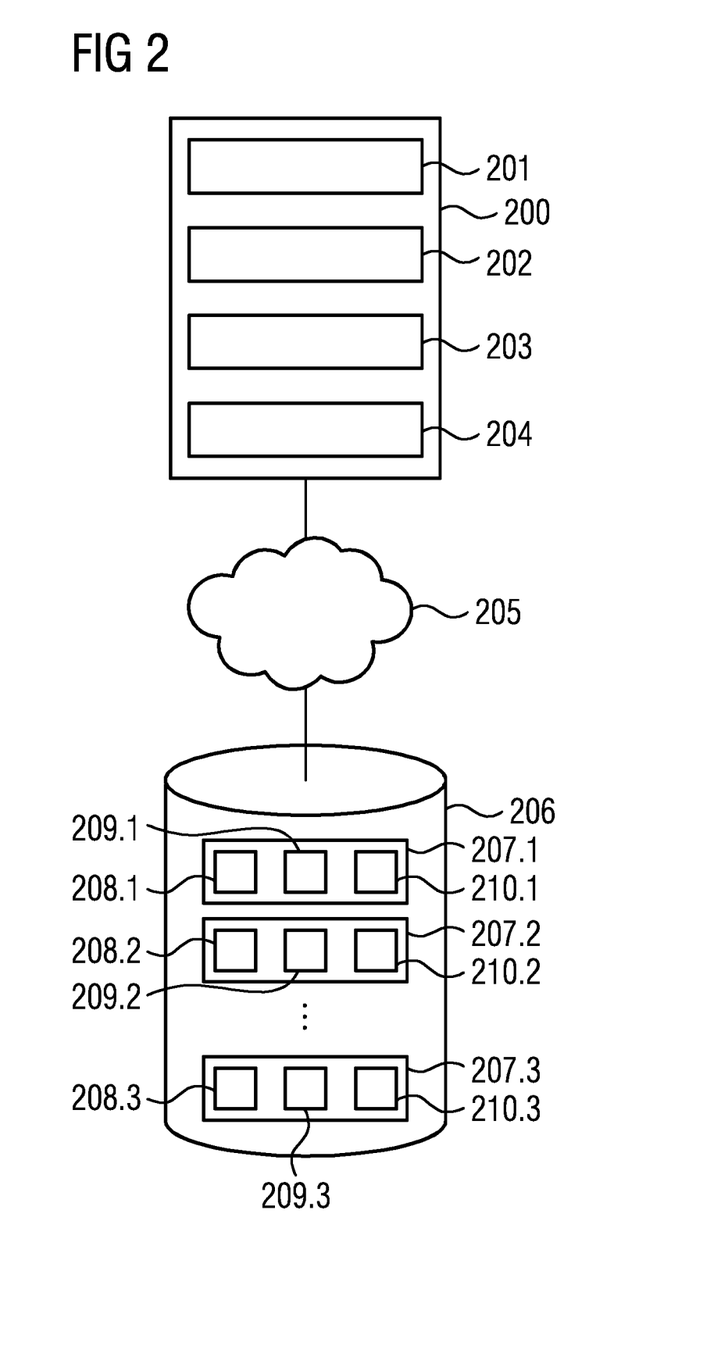
FIG. 2 schematically illustrates a parameter-determining computer according to the invention.

In the illustrated embodiment the trained imaging rule is based only on training data sets 207.1, 207.2, 207.3 which comprise training quality evaluations 210.1, 210.2, 210.3 of an operator. However, it is also possible for the imaging rule to be based on training data sets 207.1, 207.2, 207.3 which comprise training quality evaluations 210.1, 210.2, 210.3 of a particular group of operators. The group of operators can have a particular feature in common, for example the age of the operator or the specialization of doctors as operators. The training data sets 207.1, 207.2, 207.3 are saved in a database 206. In the illustrated embodiment, the database 206 is centrally localized at a different geographical location and connected via the Internet 205 to the parameter-determining computer 200. The database 206 can also be connected in a different form to the parameter-determining computer 200, however. Furthermore, the parameter-determining computer 200 can also comprise the database 206, in particular the database 206 can also be saved in the storage unit 203 of the parameter-determining computer 200.

The trained imaging rule is determined in the illustrated embodiment on a geographically remote server. The trained imaging rule is transferred before determining of the imaging parameter to the parameter-determining computer 200. The trained imaging rule can also be determined by means of the parameter-determining computer 200, however.

Other, self-learning systems, in addition to the support vector machine illustrated in this exemplary embodiment, can also be used to determine the trained imaging rule. Standard methods are known for this, such as an artificial neuronal network, or strengthening learning methods such as, for example, genetic algorithms. The use of a support vector machine is advantageous, however, because, unlike with an artificial neuronal network, the appropriate imaging parameter for a quantity of patient-specific imaging values does not need to be known during training. The use of a support vector machine is also advantageous because, unlike with a strengthening learning method, a large number of inappropriate pairs of patient-specific imaging values and imaging parameters do not have to be used in the training phase for imaging an image data set. In particular a large number of time-consuming but unusable scans do not have to be performed either.

A further step of the illustrated method is the imaging IMG of an image data set 402 by operation of a medical imaging device 300. In the illustrated embodiment this can be a computed tomography apparatus, or a magnetic resonance device, a positron-emission tomograph, an X-ray apparatus or an ultrasound device. The image data set 402 is recorded using the patient-specific imaging value and the determined imaging parameter. The recorded image data set 402 is then provided as an output after imaging. Furthermore, the duration of imaging and the radiation dose to which the patient was exposed as a result of the imaging are output by means of a result display unit 403.

A further step of the illustrated method is the determination of a quality evaluation QC by the operator. The quality of the recorded image data set 402, the duration of the imaging and the radiation dose to which the patient was exposed as a result of the imaging are emitted as outputs. Alternatively, other results of the imaging can also be added for the evaluation. In the illustrated method evaluation occurs by a binary parameter which represents whether the operator is satisfied or dissatisfied with the imaging. The evaluation can occur by means of two hardware or software keys 404, 405. Alternatively, complex evaluations can also occur, for example by way of marks or a slide rule. Alternatively, the system can derive the evaluation of the operator from whether a new imaging is carried out with the same patient-specific imaging value, but a changed imaging parameter. This case would correspond to a negative quality evaluation, while the case where no additional imaging is carried out corresponds to a positive quality evaluation.

A further step of the illustrated method is saving SAV of the result data set, including the patient-specific imaging values, imaging parameter and the quality evaluation. In the illustrated embodiment saving occurs as a supplement to the training data sets 207.1, 207.2, 207.3 in the database 206. Saving can also occur in the storage unit 203 of the parameter-determining unit 200, however.

A further step of the illustrated method is training TRN of the trained imaging rule based on the training data sets 207.1, 207.2, 207.3 and the result data set. In the illustrated method, at least one first hypersurface is determined for this purpose by means of the support vector machine, and this separates the two categories of data sets. The trained imaging rule can then be determined such that, for a given patient-specific imaging value, the imaging parameter is determined such that the data point 512, 602 including the patient-specific imaging value, and the imaging parameter has an extremal spacing from the hypersurface. Training TRN of the trained imaging rule occurs in the illustrated method on a geographically remote server. Alternatively, the trained imaging rule can also be trained by the parameter-determining computer 200, however. Training TRN of an already trained imaging rule can also be called continuous training.

FIG. 2 shows the parameter-determining computer 200. In this embodiment the parameter-determining computer 200 has an interface 201, a processor 202, a storage unit (memory) 203 and an input and output unit 204. The term "computer" means any of a console, a microcontroller or an integrated circuit. An interface 201 can be a hardware or software interface (for example PCI bus, USB or Firewire). The processor 202 can have hardware elements or software elements, for example a microprocessor or what is known as an FPGA (acronym for "Field Programmable Gate Array"). The storage unit 203 can be implemented as a Random Access Memory (RAM for short) or as a permanent mass storage device (hard disk, USB stick, SD card, Solid State Disk). An input and output unit 204 can be a separate input unit (keyboard, mouse) and a separate output unit (screen, printer). It can also be a combination of an input unit and an output unit, for example a touchscreen. The parameter-determining computer 200 is connected over a network 205 to a database 206. The network 205 can preferably be the Internet, but alternatively an Intranet or a direct connection. The database 206 is preferably implemented by a server, which can also be locally separate from the parameter-determining computer 200. The database 206 holds a large number of data sets 207.1, 207.2, 207.3. Each of the data sets 207.1, 207.2, 207.3 includes a patient-specific imaging value 208.1, 208.2, 208.3, an imaging parameter 209.1, 209.2, 209.3 and a quality evaluation 210.1, 210.2, 210.3.

In the embodiment shown here, at least one computer program is saved on the storage device 203 of the parameter-determining computer 200, and this carries out all method steps of the inventive method when the computer program is run on the processor 202. The computer program for carrying out the method steps of the inventive method comprises program code. Furthermore, the computer program can be designed as an executable data file and/or be saved on a different computing system to the parameter-determining computer 200. For example, the parameter-determining computer 200 can be designed such that the computer program for carrying out the inventive method is loaded via an Intranet or the Internet into the storage device 203 of the parameter-determining computer 200. Furthermore, in the illustrated exemplary embodiment the trained imaging rule is saved in the storage device 203 of the parameter-determining computer 200.

Figure 3:
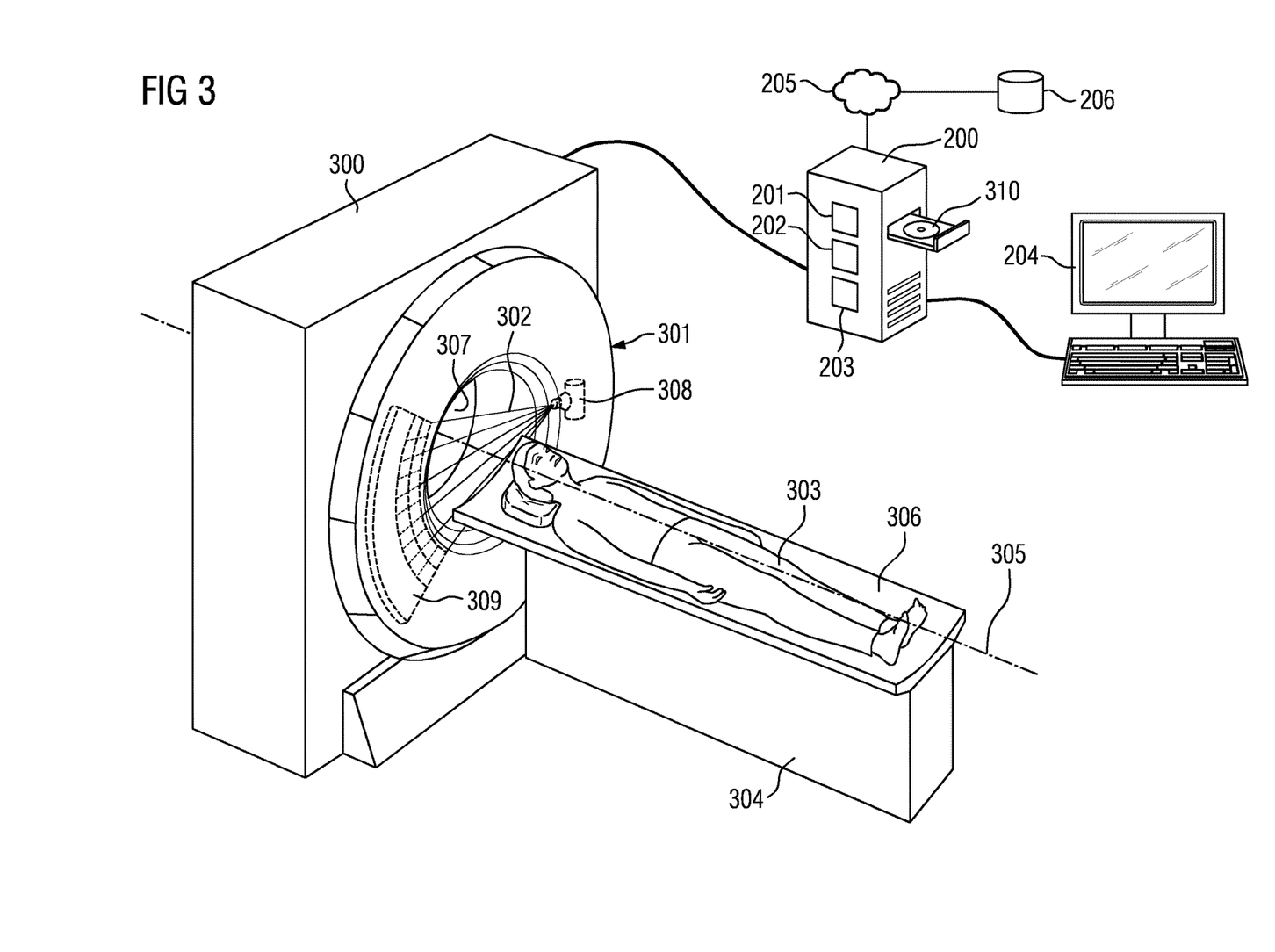
FIG. 3 shows an MR apparatus having a parameter-determining computer according to the invention.

FIG. 3 shows an imaging device, in the embodiment shown here the imaging device is a computerized tomography device 300. The computerized tomography device 300 shown here has a scanner 301 comprising an X-ray source 308 and an X-ray detector 309. The scanner 301 rotates during acquisition of scan data about a system axis 305, and the X-ray source 308 emits X-ray radiation 302 during imaging. In the example shown here the X-ray source 308 is an X-ray tube. In the example shown here the X-ray detector 309 is a line detector having a plurality of lines.

In the exemplary embodiment shown here a patient 303 lies on a patient couch 306 during acquisition of scan data. The patient couch 306 is connected to a couch base 304 such that it supports the patient couch 306 with the patient 303. The patient couch 306 is designed to move the patient 303 through the opening 307 of the scanner 301 along an imaging direction. The imaging direction is usually given by the system axis 305 about which the scanner 301 rotates during imaging of scan data. With spiral imaging, the patient couch 306 is moved continuously through the opening 307 while the scanner 301 rotates around the patient 303 and acquires scan data. The X-ray radiation 302 then describes a spiral on the surface of the patient 303. In order to determine an imaging parameter based on a patient-specific imaging value, the computerized tomography apparatus 300 shown in FIG. 3 also has a parameter-determining computer 200.

In the exemplary embodiment shown in FIG. 3 the parameter-determining computer 200, the interface 201 is a component of the computer 200. The computer 200 is connected to an input and output unit 204 in the form of a screen combined with an input device. The image data sets 402 can be displayed on the screen in various forms, for example as rendered volume images or as sectional images. The input device of the input and output unit 204 is, for example, a keyboard, a mouse, a touch screen or a microphone for speech input. The inventive computer program can be started by the input device. The individual steps of the inventive method can be supported by the input device, for example a patient-specific imaging value can be entered via the keyboard, such as the height, age, weight and gender of the patient 303.

The computer 200 and the associated units can cooperate with a computer-readable data storage medium 310, in order to implement the inventive method according to program code of the storage medium 310. The computer-readable medium can be a CD, DVD, Blu-ray disk, a memory stick or a hard disk.

Figure 4:
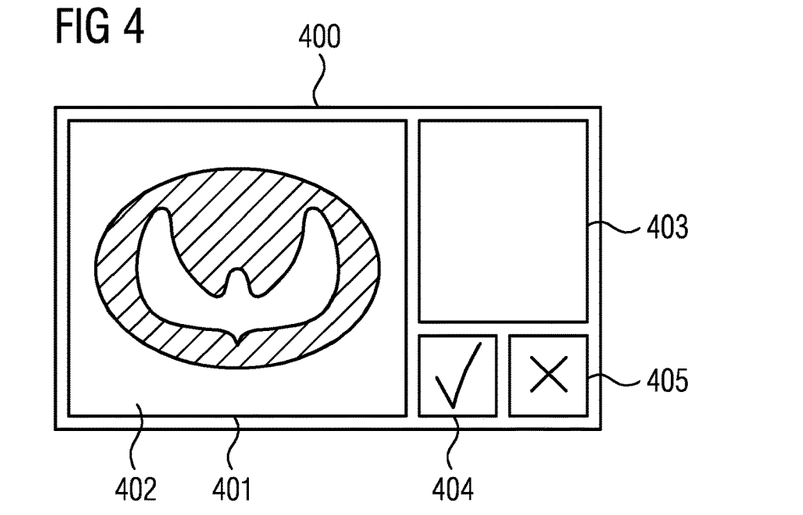
FIG. 4 shows an evaluation unit in accordance with the invention.

FIG. 4 shows a further exemplary embodiment 400 of an input and output unit 204. The illustrated input and output unit 400 is the combination of an image display unit 401 on which an image data set 402 can be displayed, having a result display unit 403 and two switches 404 and 405. The illustrated input and output unit can be a touch screen at which the image display unit 401, result display unit 403 and switches 404 and 405 are displayed in a shared screen. The image display unit 401 can include further buttons that can be used for rotation, shifting, enlargement and/or reduction of the image data set 402. Furthermore, the image display unit 401 can include buttons that are designed for choosing a particular image from the image data set 402. In particular, further data for imaging can be faded in the result display 403, in particular the duration of imaging of the image data set 402 and the radiation dose corresponding to the absorption by a patient 303. The result display unit 403 can also be embedded in the image display unit 401. Switch 404 is a button; an operator can indicate his or her satisfaction with the quality of imaging of the image data set 402 by pressing this button. Switch 405 is a button; an operator can indicate his dissatisfaction with the quality of the imaging of image data set 402 by pressing this button. The buttons 404 and 405 can also be embedded in the image display unit 401 or the result display unit 403.

Figure 5:
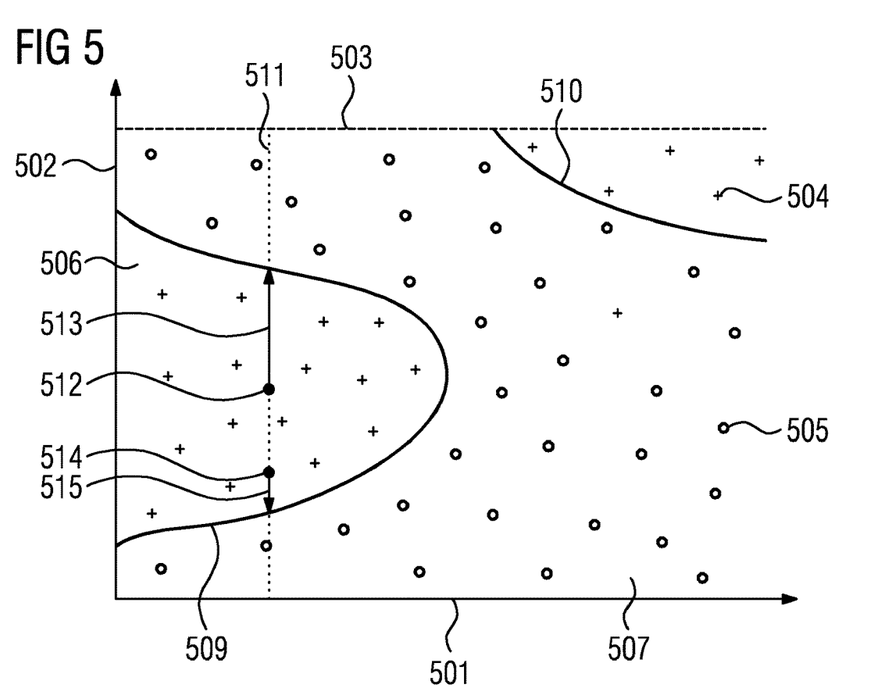
FIG. 5 shows a first parameter vector space having quality evaluations for explaining the invention.
Figure 6:
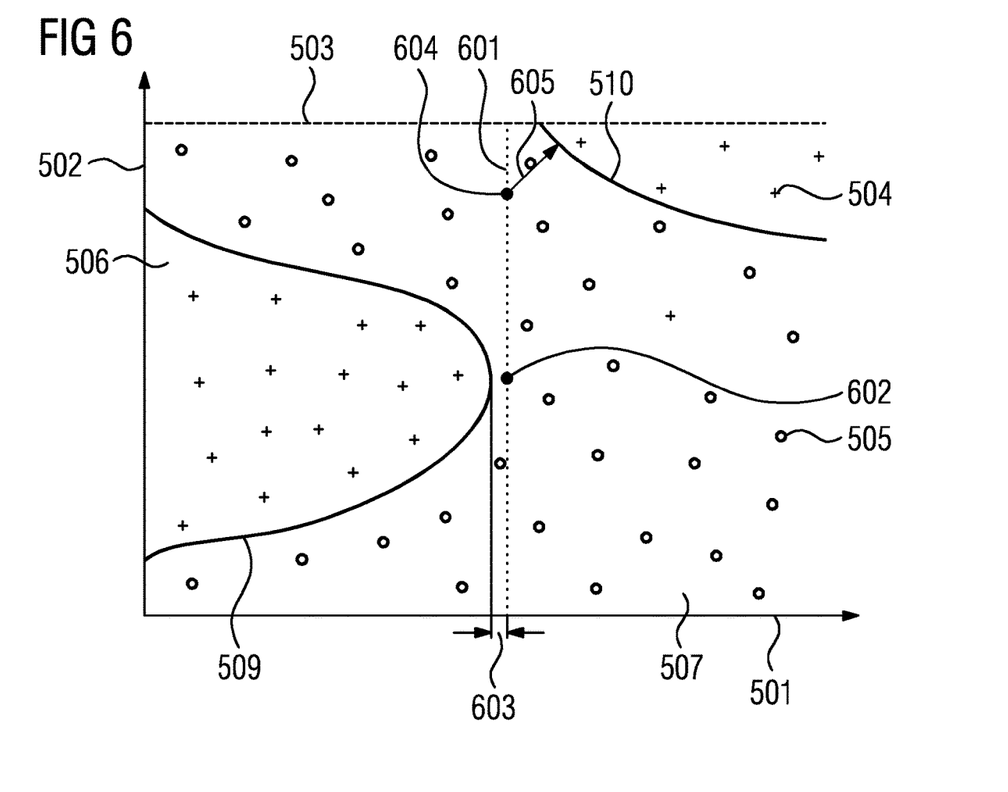
FIG. 6 shows a second parameter vector space having quality evaluations for explaining the invention.

FIG. 5 and FIG. 6 show an exemplary parameter space with quality evaluation, and an exemplary embodiment of a trained imaging rule. The coordinate axis 501 of the patient-specific imaging value and the coordinate axis 502 of the imaging parameter are plotted. In the illustrated example, the patient-specific imaging value as well as the imaging parameter are one-dimensional variables; the parameter space is therefore two-dimensional. Furthermore, the parameter space contains limits 503 of the adjustable imaging parameters. The limits 503 are specified by the properties of the scanner. For example, there is an upper limit value for the adjustable X-ray voltage and/or the adjustable X-ray current in a CT apparatus. Furthermore, the parameter space includes data points 504, 505, which are each associated with a patient-specific imaging value and an imaging parameter. A distinction is made between data points 504 with positive quality evaluation by the operator and between data points 505 with negative quality evaluation by the operator. Furthermore, the parameter space includes subspaces 506, 507, which each include predominantly only data points having uniform quality evaluation. For example, subspace 506 predominantly has data points with a positive quality evaluation, subspace 507 predominantly has data points 505 with a negative evaluation. The subspaces 506 and 507 are separated by a hypersurface 509. The parameter space also has further hypersurfaces 510 that separate further subspaces.

When determining an imaging parameter based on a patient-specific imaging value by using a trained imaging rule, a hyperplane 511, 601 is marked, which contains all data points having this patient-specific imaging value. A data point 512, 514, 602, 604 having the imaging parameter to be determined and the specified patient-specific imaging value therefore must lie on the hyperplane 511, 601.

In a first case, shown in FIG. 5, the hyperplane 511 has data points shared with a subspace 506, which predominantly contains data points 504 with positive quality evaluation. A data point 512, which belongs to the imaging parameter 502 determined by means of the trained imaging rule, then lies in a subspace 506 having data points with predominantly positive quality evaluation, and has maximum spacing 513 from the hypersurface 509, which delimits the subspace 506, and from all other hypersurfaces. Another, unsuitable data point 514 has a non-maximum spacing 515 from the hypersurface 509.

In a second case, shown in FIG. 6, the hyperplane 601 does not have data points shared with a subspace 506, which predominantly contains data points 504 with positive quality evaluation, but lies solely in a subspace 507 that contains predominantly data point 505 with negative quality evaluation. A data point 602, which belongs to the imaging parameter 502 determined with the trained imaging rule, then lies in the subspace 507 having data points with predominantly negative quality evaluation, and has minimum spacing 603 from the closest hypersurface 509, which delimits the subspace 507. Another, unsuitable data point 604 has a non-maximum spacing 605 from the closest hypersurface 510.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for determining an imaging parameter for use in operating an imaging apparatus, said method comprising:

provision a computer with a patient-specific imaging value for an image dataset to be acquired from the patient;

in said computer, determining an imaging parameter for operating an imaging apparatus in order to acquire said image data set, by applying a trained imaging rule to the patient-specific imaging value, said trained imaging rule being based on a plurality of training data sets, with each training data set comprising at least one patient-specific training imaging value and at least one training imaging parameter and at least one training quality evaluation;

from said computer, operating said imaging apparatus according to said imaging parameter in order to acquire said image data set from the patient;

in said computer, conducting a quality evaluation of the acquired image data set and the patient-specific imaging value and the imaging parameter, in order to obtain a result data set;

in said computer, conducting said quality evaluation in order to produce a measure of at least one of a quality of said image data set, a duration required for operating said imaging apparatus in order to acquire the image data set, and a radiation dose used by said imaging apparatus in order to acquire said image data set; and storing the result data set in a memory accessible by said computer;

conducting said quality evaluation in order to produce a measure of at least one of a quality of said image data set, a duration required for operating said imaging apparatus in order to acquire the image data set, and a radiation dose used by said imaging apparatus in order to acquire said image data set.

2. A method as claimed in claim 1 comprising:
in said computer, training said trained imaging rule using said training data sets and the stored result data set.

3. A method as claimed in claim 1 comprising producing, as said measure, a discrete parameter that can assume only a finite number of values.

4. A method as claimed in claim 3 comprising generating said measure as a discrete parameter that can assume exactly two different values.

5. A method as claimed in claim 3 comprising determining said trained imaging rule in said computer by applying a support vector machine in said computer to said training data sets so as to sort at least some of said training data sets dependent on said discrete parameter into at least one first category and one second category, and determining a parameter space of all combinations of patient-specific imaging values and imaging parameters so as to include at least one hypersurface that separates said first and second categories, and determining said trained imaging rule dependent on said hypersurface.

6. A method as claimed in claim 5 comprising determining said trained imaging rule in said computer dependent on said hypersurface by mapping a patient-specific imaging value on the imaging parameter so as to make a spacing between said hypersurface and a data point extreme, said data point comprising the patient-specific imaging value and the determined imaging parameter.

7. A method as claimed in claim 1 comprising conducting said training quality evaluation in said computer so as to produce a measure of at least one of a quality of said image data set, a duration required for operating said imaging apparatus in order to acquire the image data set, and a radiation dose used by said imaging apparatus in order to acquire said image data set.

8. A method as claimed in claim 7 comprising producing, as said measure, a discrete parameter that can assume only a finite number of values.

9. A method as claimed in claim 8 comprising generating said measure as a discrete parameter that can assume exactly two different values.

10. A method as claimed in claim 8 comprising determining said trained imaging rule in said computer by applying a support vector machine in said computer to said training data sets so as to sort at least some of said training data sets dependent on said discrete parameter into at least one first category and one second category, and determining a parameter space of all combinations of patient-specific imaging values and imaging parameters so as to include at least one hypersurface that separates said first and second categories, and determining said trained imaging rule dependent on said hypersurface.

11. A method as claimed in claim 10 comprising determining said trained imaging rule in said computer dependent on said hypersurface by mapping a patient-specific imaging value on the imaging parameter so as to make a spacing between said hypersurface and a data point extreme, said data point comprising the patient-specific imaging value and the determined imaging parameter.

12. A parameter-determining computer for determining an imaging parameter for use in operating an imaging apparatus, said computer comprising:
an input interface that receives a patient-specific imaging value for an image dataset to be acquired from the patient;
a processor in communication with said input interface, said processor determining an imaging parameter for operating an imaging apparatus in order to acquire said image data set, by applying a trained imaging rule to the patient-specific imaging value, said trained imaging rule being based on a plurality of training data sets, with each training data set comprising at least one patient-specific training imaging value and at least one training imaging parameter and at least one training quality evaluation;
an output interface in communication with said processor;
said processor, via said output interface, operating said imaging apparatus according to said imaging parameter in order to acquire said image data set from the patient;
said processor conducting a quality evaluation of the acquired image data set and the patient-specific imaging value and the imaging parameter, in order to obtain a result data set;
said processor conducting said quality evaluation in order to produce a measure of at least one of a quality of said image data set, a duration required for operating said imaging apparatus in order to acquire the image data set, and a radiation dose used by said imaging apparatus in order to acquire said image data set; and
said processor storing the result data set in a memory accessible by the processor.

13. A parameter-determining computer as claimed in claim 12, wherein said processor circuitry forms a support vector machine.

14. A non-transitory, computer-readable data storage medium encoded with programming instructions, said storage medium being loaded into a computer and said programming instructions causing said computer to:
receive a patient-specific imaging value for an image dataset to be acquired from the patient;
determine an imaging parameter for operating an imaging apparatus in order to acquire said image data set, by applying a trained imaging rule to the patient-specific imaging value, said trained imaging rule being based on a plurality of training data sets, with each training data set comprising at least one patient-specific training imaging value and at least one training imaging parameter and at least one training quality evaluation;
operate said imaging apparatus according to said imaging parameter in order to acquire said image data set from the patient;
conduct a quality evaluation of the acquired image data set and the patient-specific imaging value and the imaging parameter, in order to obtain a result data set;
conduct said quality evaluation in order to produce a measure of at least one of a quality of said image data set, a duration required for operating said imaging apparatus in order to acquire the image data set, and a radiation dose used by said imaging apparatus in order to acquire said image data set; and
store the result data set in a memory accessible by said computer.

15. An imaging apparatus comprising:
an image data acquisition scanner;
a computer provided with a patient-specific imaging value for an image dataset to be acquired from the patient;
said computer comprising processor circuitry that determines an imaging parameter for operating said image data acquisition scanner in order to acquire said image data set, by applying a trained imaging rule to the patient-specific imaging value, said trained imaging rule being based on a plurality of training data sets, with each training data set comprising at least one patient-specific training imaging value and at least one training imaging parameter and at least one training quality evaluation;

said computer operating said imaging apparatus according to said imaging parameter in order to acquire said image data set from the patient;

said computer operating said processor circuitry to conduct a quality evaluation of the acquired image data set and the patient-specific imaging value and the imaging parameter, in order to obtain a result data set;

said computer operating said processor circuitry to conduct said quality evaluation in order to produce a measure of at least one of a quality of said image data set, a duration required for operating said imaging apparatus in order to acquire the image data set, and a radiation dose used by said imaging apparatus in order to acquire said image data set; and a memory accessible by said computer in which said computer stores said result data set.

16. An imaging apparatus as claimed in claim 15, wherein said computer operates said processor circuitry to train said trained imaging rule using said training data sets and the stored result data set.

17. An imaging apparatus as claimed in claim 15, wherein said processor circuitry forms a support vector machine.

* * * * *